US00PP13439P2

(12) United States Plant Patent
Vandenberg

(10) Patent No.: US PP13,439 P2
(45) Date of Patent: Dec. 31, 2002

(54) CHRYSANTHEMUM PLANT NAMED 'SHARP'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/900,102

(22) Filed: Jul. 9, 2001

(51) Int. Cl.[7] ..... A01H 5/00

(52) U.S. Cl. ..... Plt./287

(58) Field of Search ..... Plt./287, 288, 289

*Primary Examiner*—Howard J. Locker
(74) *Attorney, Agent, or Firm*—C. A. Whealy

(57) ABSTRACT

A distinct cultivar of Chrysanthemum plant named 'Sharp', characterized by its quilled decorative-type inflorescences that are about 5.1 cm in diameter; attractive white-colored inflorescences with green centers; response time about 58 days; freely flowering habit; dark green foliage; and excellent postproduction longevity with inflorescences maintaining good substance and color for about three weeks in an interior environment.

2 Drawing Sheets

BACKGROUND OF THE INVENTION

The present invention relates to a new and distinct cultivar of Chrysanthemum plant, botanically known as *Chrysanthemum×morifolium* and hereinafter referred to by the name 'Sharp'.

The new Chrysanthemum is a product of a planned breeding program conducted by the Inventor in Salinas, Calif. and Alva, Fla. The objective of the breeding program is to create new cut Chrysanthemum cultivars having inflorescences with desirable colors and good form and substance.

The new Chrysanthemum originated from a cross made by the Inventor in November, 1997, in Salinas, Calif., of a proprietary Chrysanthemum seedling selection identified as code number E917, not patented, as the female, or seed, parent with a proprietary Chrysanthemum seedling selection identified as E789, not patented, as the male, or pollen, parent.

The cultivar Sharp was discovered and selected by the Inventor as a flowering plant within the progeny of the stated cross in a controlled environment in Alva, Fla., in November, 1998. The selection of this plant was based on its desirable inflorescence color and good form and substance.

Asexual reproduction of the new Chrysanthemum by terminal cuttings taken in a controlled environment in Alva, Fla. since February, 1999, has shown that the unique features of this new Chrysanthemum are stable and reproduced true to type in successive generations.

SUMMARY OF THE INVENTION

Plants of the cultivar Sharp have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sharp'. These characteristics in combination distinguish 'Sharp' as a new and distinct cultivar:

1. Upright cut Chrysanthemum that is usually grown as a natural spray.

2. Freely flowering habit, about 11 inflorescences per flowering stem.

3. Quilled decorative-type inflorescences that are about 5.1 cm. in diameter.

4. Attractive white-colored inflorescences with green centers.

5. Response time about 58 days.

6. Dark green foliage.

7. Excellent postproduction longevity with inflorescences maintaining good substance and color for about three weeks in an interior environment.

Compared to plants of the female parent, the seedling selection identified as code number E917, plants of the new Chrysanthemum have smaller inflorescences. In addition, plants of the new Chrysanthemum and the female parent differ in ray floret color as plants of the female parent have white-colored inflorescences with light pink centers.

Plants of the male parent, the seedling selection identified as code number E789, and the new Chrysanthemum differ primarily in inflorescence color as inflorescences of the male parent are cream-white with less intense green-colored centers.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Sharp' grown as a natural spray.

The photograph on the second sheet comprises a close-up view of a typical flowering stem of 'Sharp' grown as a natural spray.

DETAILED BOTANICAL DESCRIPTION

In the following description, color references are made to The Royal Horticultural Society Colour Chart except where general terms of ordinary dictionary significance are used. The aforementioned photographs and following observations and measurements describe plants grown in La Ceja, Antioquia, Colombia, South America, under conditions which approximate commercial practice in a single-layer polyethylene-covered greenhouse. Two-week old rooted cuttings were planted on Dec. 26, 2000 and received 14 long day/short nights followed by short day/long nights until flowering. Plants were grown as single-stem natural spray cut Chrysanthemums. During the production time, the following environmental conditions were measured: day temperatures, 20 to 27° C.; night temperatures, 8 to 13° C.; and light levels, 4,000 to 6,000 foot-candles. Measurements and numerical values represent averages for six to ten typical flowering stems and were taken about 9 to 10 weeks after the start of short days.

Botanical classification: *Chrysanthemum×morifolium* cultivar Sharp.

Commercial classification: Quilled decorative-type cut Chrysanthemum.

Parentage:

*Female or seed parent.*—Proprietary *Chrysanthemum×morifolium* seedling selection identified as code number E917, not patented.

*Male or pollen parent.*—Proprietary *Chrysanthemum×morifolium* seedling selection identified as code number E789, not patented.

Propagation:

*Type.*—Terminal tip cuttings.

*Time to rooting.*—About 10 to 14 days with soil temperatures of 18 to 21° C.

*Root description.*—Fine, fibrous and well-branched.

Plant description:

*Appearance.*—Herbaceous quilled decorative-type cut flower that is typically grown as a natural spray.

*Flowering stem description.*—Aspect: Erect. Length: About 100 cm. Diameter (natural spray diameter): About 13.5 cm. Diameter (base of stem): About 5.5 mm. Internode length: About 3.75 cm. Texture: Densely pubescent; longitudinally ridged. Color: 146A.

*Foliage description.*—Arrangement: Alternate. Length: About 8.5 cm. Width: About 5.2 cm. Apex: Cuspidate. Base: Mostly truncate. Margin: Palmately lobed; sinuses mostly parallel. Texture: Upper and lower surfaces pubescent; smooth and leathery; veins prominent on lower surface. Color: Young foliage upper surface: Darker than 147A. Young foliage lower surface: Darker than 147B. Mature foliage upper surface: 147A. Mature foliage lower surface: Close to 147B. Venation, upper and lower surfaces: 147B. Petiole: Length: About 1.8 cm. Diameter: About 3 mm. Color: Upper surface: 147B. Lower surface: 147B to 147C.

Flowering description:

*Appearance.*—Decorative-type inflorescence form with elongated quilled-shaped ray florets. Inflorescences borne on terminals, arising from leaf axils. Disc and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 58 days later when grown as a natural spray.

*Postproduction longevity.*—In an interior environment, flowering stems will maintain good color and substance for about three weeks in an interior environment after one week of cool storage.

*Quantity of inflorescences.*—Freely flowering habit, about 11 inflorescences per stem develop.

*Inflorescence size.*—Diameter: About 5.1 cm. Depth (height): About 2.1 cm. Diameter of disc: No disc florets observed. Diameter of receptacle: About 6.5 mm.

*Inflorescence buds.*—Shape: Flattened sphere. Height: About 7 mm. Diameter: About 9 mm. Color: Close to 137A.

*Ray florets.*—Shape: Elongated, quilled; flattened. Length: About 2.7 cm. Width: About 3.5 mm. Corolla tube length: About 2.5 cm. Apex: Emarginate. Base: Fused. Texture: Satiny, smooth, glabrous; slightly longitudinally ridged. Aspect: Initially upright; when mature, about 45° from vertical; straight. Number of ray florets per inflorescence: About 279 arranged in numerous rows. Color: When opening: 144A to 144B, which gives a green appearance to the center of the inflorescences. Mature, throat and tube: Close to 155D; apices tipped with 144A to 144B; color does not fade with subsequent development.

*Peduncles.*—Length: First peduncle: About 3 cm. Fourth peduncle: About 7.25 cm. Seventh peduncle: About 11.75 cm. Diameter: About 2 mm. Angle: About 40 to 45° from vertical. Strength: Very strong. Texture: Pubescent. Color: 146A to 144A.

*Reproductive organs.*—Gynoecium: Present on ray florets.

*Seed.*—Seed production has not been observed.

Disease/pest resistance: Resistance to pathogens and pests common to Chrysanthemums has not been observed on plants grown under commercial conditions.

Temperature tolerance: Plants of the new Chrysanthemum have demonstrated good tolerance to low temperatures of 5° C. Plants of the new Chrysanthemum do not tolerate high temperatures greater than 40° C.

It is claimed:

1. A new and distinct cultivar of Chrysanthemum plant named 'Sharp', as illustrated and described.

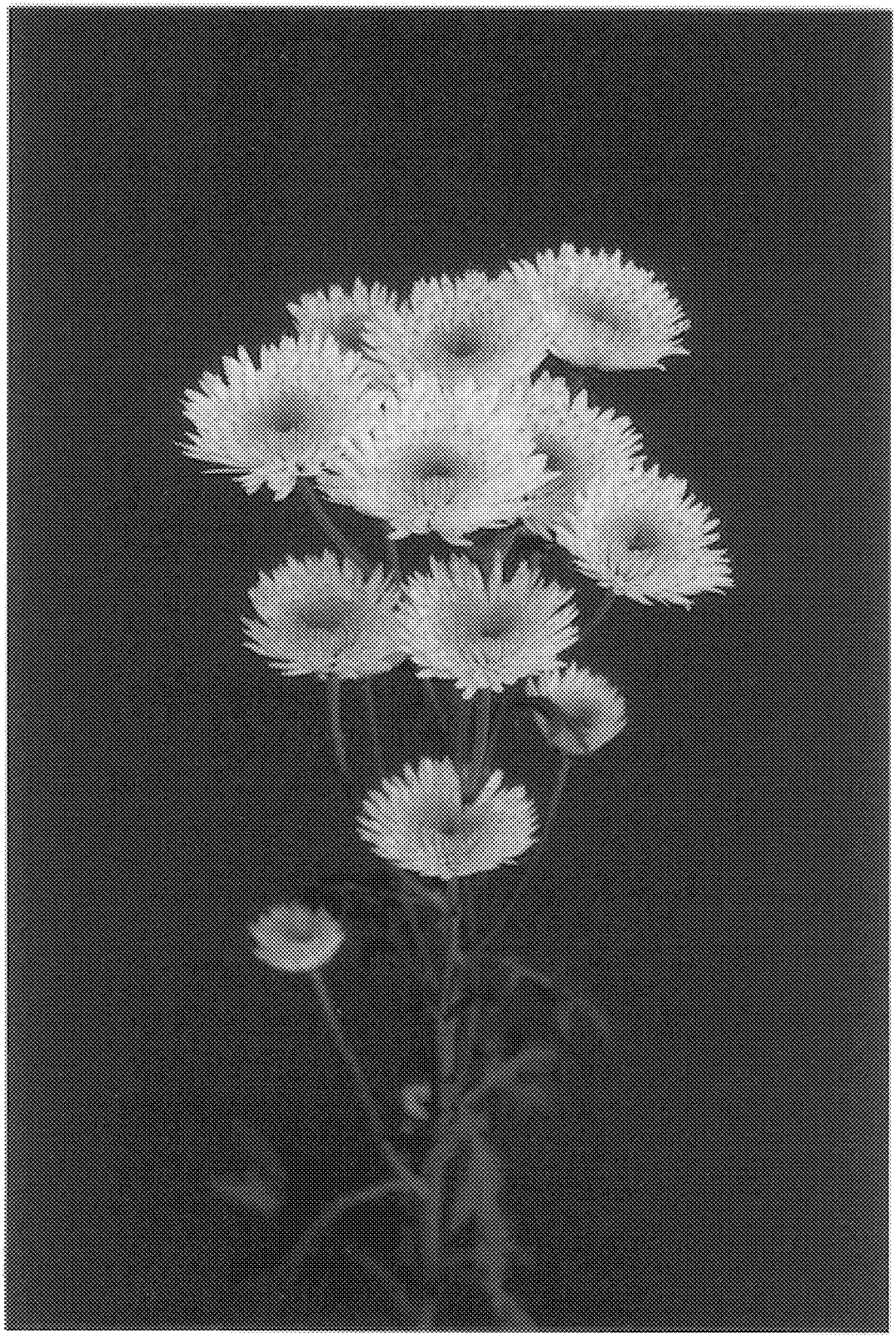

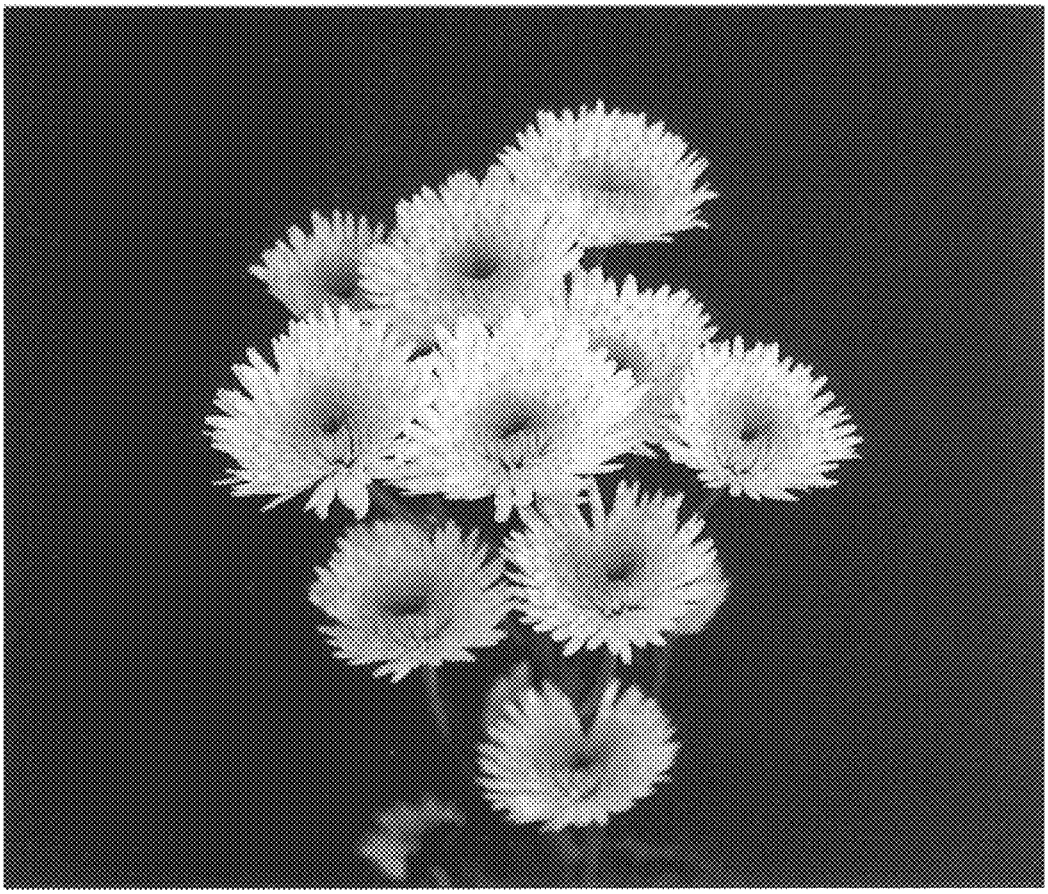

* * * * *